United States Patent [19]

Greif et al.

[11] Patent Number: 5,420,207
[45] Date of Patent: May 30, 1995

[54] PREPARATION OF POLYISOBUTYLSUCCINIC ANHYDRIDES

[75] Inventors: Norbert Greif, Bobenheim; Knut Oppenlaender, Ludwigshafen, both of Germany

[73] Assignee: BASF Aktiengesellschaft, Ludwigshafen, Germany

[21] Appl. No.: 261,032

[22] Filed: Jun. 14, 1994

[30] Foreign Application Priority Data

Jun. 14, 1993 [DE] Germany .................. 43 19 671.3

[51] Int. Cl.$^6$ .......................................... C08F 267/04
[52] U.S. Cl. ................................. 525/285; 44/333; 526/216; 526/271; 526/272; 549/255
[58] Field of Search ............... 525/285; 526/216, 271, 526/272; 549/255; 44/333; 252/51.5 A

[56] References Cited

U.S. PATENT DOCUMENTS

| | | | |
|---|---|---|---|
| 4,086,251 | 4/1978 | Cengel et al. | 549/255 |
| 4,235,786 | 11/1980 | Wisotsky | 560/203 |
| 4,282,157 | 8/1981 | van der Voort | 525/285 X |
| 4,859,210 | 8/1989 | Franz et al. | 44/53 |

FOREIGN PATENT DOCUMENTS

| | | |
|---|---|---|
| 0014288 | 8/1980 | European Pat. Off. |
| 0355895 | 2/1990 | European Pat. Off. |
| 0542380 | 5/1993 | European Pat. Off. |
| 944136 | 12/1963 | United Kingdom |

*Primary Examiner*—John Kight, III
*Assistant Examiner*—Shelley A. Dodson
*Attorney, Agent, or Firm*—Oblon, Spivak, McClelland, Maier & Neustadt

[57] ABSTRACT

Polyisobutylsuccinic anhydrides having an average molar ratio of succinic anhydride groups to polyisobutyl groups of from 1.05:1 to 1.3:1 are prepared by reacting polyisobutene having an average molecular weight $M_w$ of 600–5000 and containing at least 70% of terminal double bonds with maleic anhydride in a molar ratio of maleic anhydride to polyisobutene of from 1.05:1 to 3:1 at 160°–210° C. in the presence of a catalytic amount of a dicarboxylic acid of 2 to 6 carbon atoms.

5 Claims, No Drawings

PREPARATION OF POLYISOBUTYLSUCCINIC ANHYDRIDES

The present invention relates to a improved process for the preparation of polyisobutylsuccinic anhydrides having an average molar ratio of succinic anhydridge groups to polyisobutyl groups of from 1.05:1 to 1.3:1.

Polyisobutylsuccinimides are widely used as ashless dispersants in the lubricant sector. They are contained in oils for gasolene and diesel engines in amounts of up to 10% by weight and are intended therein to prevent the agglomeration of particles which is generally referred to as sludge formation. The dispersing effect of these additives is the most important property for this application.

Polyisobutylsuccinimides are generally prepared from the corresponding anhydrides.

Polyisobutylsuccinic anhydrides in turn are usually prepared from polyisobutenes and maleic anhydride. In order to increase the yield, this reaction is frequently carried out in the presence of chlorine, resulting in a chlorine-containing reaction product. Such products are now undesirable since they may promote corrosion, owing to their secondary constituents.

A purely thermal reaction of the polyisobutene and maleic anhydride may lead to chlorine-free products. However, according to EP-A 457 599, relatively high temperatures substantially above 200° C. in conjunction with superatmospheric pressure are required in order to achieve economical reaction times. These reaction conditions result in tar formation, which lowers the quality of the product. Tar-containing products lead to the undesirable formation of insoluble components in the lubricant.

JP-A 89/79 163 describes a process for the preparation of alkenylsuccinic anhydrides by reacting olefins, such as α-olefins of not more than 30 carbon atoms, with maleic anhydride in the presence of carboxylic acids as catalysts.

In order to use polyisobutylsuccinic anhydrides as lubricant additives, a certain degree of bismaleation is desirable, ie. the products carry on average more than one succinic anhydride group per polyisobutene unit.

It is an object of the present invention to provide an improved process for the preparation of polyisobutylsuccinic anhydrides having an average molar ratio of succinic anhydride groups to polyisobutyl groups of from 1.05:1 to 1.3:1, which makes it possible to obtain, under mild reaction conditions, products which are substantially tar-free.

We have found that this object is achieved by an improved process for the preparation of polyisobutylsuccinic anhydrides having an average molar ratio of succinic anhydride groups to polyisobutyl groups of from 1.05:1 to 1.3:1, wherein polyisobutene having an average molecular weight $M_w$ of 600–5000 and containing at least 70% of terminal double bonds is reacted with maleic anhydride in a molar ratio of maleic anhydride to polyisobutene of from 1.05:1 to 3:1 at 160°–210° C. in the presence of a catalytic amount of a dicarboxylic acid of 2 to 6 carbon atoms.

The polyisobutenes to be used according to the invention are known (for example from EP-A 145 235) and have a molecular weight $M_w$ of 600–5000, preferably 800–1200, and contain at least 70%, preferably 80–90%, of terminal double bonds. In comparison with internal double bonds, these terminal double bonds are particularly reactive in reactions with maleic anhydride.

For the preparation of the products, it is necessary for 1 equivalent of polyisobutene to react with, on average, more than 1 equivalent of maleic anhydride (ie. bismaleation). The ene reaction between polyisobutene and maleic anhydride leads initially to a product which carries a reactive double bond in the polyisobutyl radical. This permits a further ene reaction with maleic anhydride to give the bismaleated product.

The starting materials are reacted in a molar ratio of from 1.05:1 to 3:1, preferably from 1.1:1 to 2:1, of maleic anhydride to polyisobutene.

The reaction is carried out in the presence of a catalytic amount of a dicarboxylic acid of 2 to 6 carbon atoms. The acids are preferably aliphatic compounds, such as oxalic acid, maleic acid, fumaric acid and adipic acid, or mixtures of these compounds. Oxalic acid and mixtures of oxalic acid and maleic acid are preferred. The dicarboxylic acids may be added to the reaction batch. However, maleic acid may also be formed from maleic anhydride under the reaction conditions by the addition of appropriate amounts of water. The amounts of catalyst are as a rule from 1 to 10, preferably from 3 to 8, mol %, based on polyisobutene.

The reaction is carried out at 160°–210° C. The pressure during the reaction is in general atmospheric pressure, but it is also possible to employ the autogenous pressure of the reaction mixture or superatmospheric pressure.

The reaction can be carried out in the presence or absence of a solvent. Particular examples of these are hydrocarbons, such as naphtha and petroleum (boiling range, for example, 170°–210°C.), and ethers, such as dimethyl diglycol and diethyl diglycol. However, the products themselves are also suitable solvents. The amount of solvent used is usually from 20 to 50% by weight, based on the reaction batch.

The starting materials may be mixed before the reaction and reacted at the reaction temperature. In a further embodiment, only some of the maleic anhydride is initially taken and the remaining part is added to the reaction mixture at the reaction temperature so that a homogeneous phase is always present in the reaction vessel.

Depending on the reaction temperature chosen, the reaction is complete, as a rule, after from 3 to 10 hours. The mixture is then worked up in a manner known per se in order to obtain the product. This is generally done by distilling off all volatile components and isolating the distillation residue.

The polyisobutylsuccinic anhydrides prepared by the novel process are obtained in substantially tar-free form, which permits further processing of the products without additional purification measures.

The polyisobutylsuccinic anhydrides prepared by the novel process are used as intermediates for the preparation of polyisobutylsuccinamides and polyisobutylsuccinimides. These products are obtained in a manner known per se, by reacting polyisobutylsuccinic anhydrides with a primary or secondary amine with elimination of water.

These amines may in principle be any compounds suitable for imide formation, such as ammonia, mono- and dialiphatic amines and cycloaliphatic and aromatic amines. In view of the use of the products as lubricant additives, however, polyamines are preferred. The polyamines preferably carry from 2 to 10 nitrogen atoms. Polyamines which carry alkylene groups,-such as ethylene, 1,2-propylene, 2,2-dimethylpropylene, eg. ethylenediamine, diethylenetriamine, triethylenetetramine, tetraethylenepentamine, dipropylenetriamine and tripropylenetetramine, are particularly preferred.

The polyisobutylsuccinamides and polyisobutylsuccinimides thus obtainable are used as additives for gasoline fuels, rotary piston engine fuels and diesel fuels, in particular for fuels in gasoline engines, preferably in amounts of from 20 to 300 ppm, based on the fuel, of pure active substance. They may also be used in combination with other dispersants, such as polyisobutylamines They are furthermore suitable as lubricant additives, in particular for mineral, semisynthetic and completely synthetic engine oils. They are used in the engine oils preferably in amounts from 1 to 10% by weight, based on the oil.

EXAMPLES

General Preparation Method

Polyisobutene (PIB) having an average molecular weight $M_w$ of 900 and containing 85% of terminal double bonds was heated with maleic anhydride (MAA) in the presence of a mol% (based on PIB) of a dicarboxylic acid for 10 hours at a temperature T. After isolation of the product, the saponification value (SV), the molar ratio of succinic anhydride groups to polyisobutyl groups (degree of bismaleation) and, in some experiments, the tar content were determined (for further reaction data: cf. table).

In order to determine the tar content, the reaction residue was taken up in hexane and the tar was filtered off.

| Experiment | mol of MAA/ mol of PIB | T [°C.] | a [mol %] | Dicarboxylic acid | (SV) [mg of KOH/ g of product] | Degree of bismaleation | Tar [% by weight] |
|---|---|---|---|---|---|---|---|
| 1 | 2.0 | 190 | i) 2.5 and ii) 5.0 | i) Oxalic acid ii) Maleic acid | 108 | 1.22 | 0.12 |
| 2 | 2.0 | 210 | i) 2.5 and ii) 5.0 | i) Oxalic acid ii) Maleic acid | 116 | 1.29 | 0.20 |
| Comparison 1 | 1.8 | 190 | — | — | 104 | 1.13 | 0.98 |
| 3 | 2.0 | 195 | 5.0 | Maleic acid | 113 | 1.28 | * |
| 4 | 2.0 | 190 | 5.0 | Oxalic acid | 106 | 1.18 | * |
| 5 | 1.8 | 192 | 5.0 | Maleic acid | 96 | 1.05 | * |
| 6 | 1.8 | 195 | 4.5 | Fumaric acid | 112 | 1.23 | * |
| 7 | 1.8 | 195 | 7.5 | Maleic acid | 109 | 1.24 | * |
| Comparison 2 | 2.0 | 195 | — | — | 123 | 1.38 | * |
| Comparison 3 | 1.8 | 210 | — | — | 134 | 1.43 | 1.05 |
| Comparison 4 | 2.0 | 210 | — | — | 144 | 1.56 | * |

* not determined

Experiments 1 and 2 and Comparative Experiment 1 show that the novel process leads to a dramatic reduction in the tar content of the product.

Experiments 3-7 and Comparative Experiments 2-4 show that the novel experiments lead to the desired degree of bismaleation and a low tar content in contrast to a reaction without a catalyst or to a reaction without a catalyst and additionally at elevated temperatures.

We claim:

1. A process for the preparation of polyisobutylsuccinic anhydrides having an average molar ratio of succinic anhydride groups to polyisobutyl groups of from 1.05:1 to 1.3:1, wherein polyisobutene having an average molecular weight $M_w$ of 600–5000 and containing at least 70% of terminal double bonds is reacted with maleic anhydride in a molar ratio of maleic anhydride to polyisobutene of from 1.05:1 to 3:1 at 160° -210° C. in the presence of a catalytic amount of from 1 to 10 mol %, based on polyisobutene, of a dicarboxylic acid of 2 to 6 carbon atoms.

2. A process as claimed in claim 1, wherein the average molecular weight $M_w$ of the polyisobutene is from 800 to 1200.

3. A process as claimed in claim 1, wherein the content of terminal double bonds in the polyisobutene is 80-90%.

4. A process as claimed in claim 1, wherein the dicarboxylic acid used is oxalic acid.

5. A process as claimed in claim 1, wherein the dicarboxylic acid is present in an amount of 3 to 8 mol % based on polyisobutene.

* * * * *